United States Patent [19]

Griffiths et al.

[11] Patent Number: 5,486,617
[45] Date of Patent: Jan. 23, 1996

[54] PROCESS FOR THE PREPARATION OF 2-SUBSTITUTED 5-CHLOROIMIDAZOLE-4-CARBALDEHYDES

[75] Inventors: Gareth Griffiths, Visp; René Imwinkelried, Brig-Glis; Jacques Gosteli, Basel, all of Switzerland

[73] Assignee: Lonza Ltd., Gampel/Valais, Switzerland

[21] Appl. No.: 340,377

[22] Filed: Nov. 14, 1994

[30] Foreign Application Priority Data

Nov. 15, 1993 [CH] Switzerland .............................. 3410/93

[51] Int. Cl.⁶ .................................................. C07D 233/68
[52] U.S. Cl. ........................................................ 548/333.5
[58] Field of Search ............................................ 548/333.5

[56] References Cited

U.S. PATENT DOCUMENTS 4,355,040  10/1982  Furukawa et al. ...................... 424/273

FOREIGN PATENT DOCUMENTS 0028834  5/1981  European Pat. Off. .
2804435  8/1978  Germany .

*Primary Examiner*—Patricia L. Morris
*Attorney, Agent, or Firm*—Fisher, Christen & Sabol

[57] ABSTRACT

A process for preparing 2-substituted 5-chloroimidazole-4-carbaldehydes of the general formula:

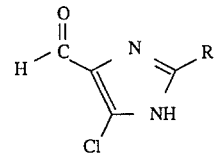

In the process, a glycine ester hydrohalide is ring-closed with an imidate ester to obtain the intermediate 2-substituted 3,5-dihydroimidazol-4-one. This intermediate is converted with an N,N-substituted formamide acetal into an N,N-substituted aminomethyleneimidazolinone. This latter intermediate is chlorinated with phosphorus oxychloride or phosgene to obtain the final product 2-substituted 5-chlorimidazole-4-carbaldehydes of the general formula I.

Also disclosed are N,N-substituted aminomethyleneimidazolinones of the general formula:

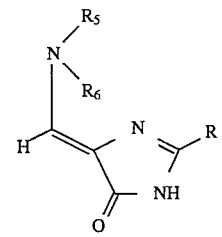

wherein R is hydrogen or is an alkyl group, an alkenyl group, a cycloalkyl group, an arylalkyl group or an aryl group, and $R_5$ and $R_6$ are identical or different and each is an alkyl group or an aryl group, in the form of the E- or Z-isomer.

12 Claims, No Drawings

PROCESS FOR THE PREPARATION OF 2-SUBSTITUTED 5-CHLOROIMIDAZOLE-4-CARBALDEHYDES

BACKGROUND OF THE INVENTION

1. Field of the Invention

The invention relates to a novel process for preparing 2-substituted 5-chloroimidazole-4-carbaldehydes of the general formula:

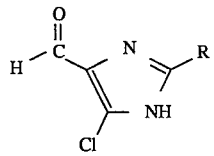

wherein R is hydrogen, an alkyl group, an alkenyl group, a cycloalkyl group, an arylalkyl group or an aryl group.

2. Background Art

Several methods for preparing 2-substituted 5-chloroimidazole-4-carbaldehydes of the general formula I are known in the art.

U.S. Pat. No. 4,355,040 discloses a process in which 2-amino-3,3-dichloroacrylonitrile is reacted both with an aldehyde to obtain the corresponding azomethine intermediate, and further with a halohydrocarbon and water to obtain the 2-substituted 5-haloimidazole-4-carbaldehyde. It should be noted that experimental details are lacking in the patent specification. And, a great disadvantage of this synthesis is that the starting 2-amino-3,3-dichloroacrylonitrile first has to be prepared by reacting dichloroacetonitrile with hydrocyanic acid/sodium cyanide. The dichloroacetonitrile and hydrocyanic acid/sodium cyanide reactants are extremely toxic reactants. The safety measures which are necessary even to prepare these starting materials make the entire process unsuitable on an industrial scale.

U.S. Pat. No. 4,355,040 also discloses a variant 3-stage process in which, in the first stage, an amidine hydrochloride is ring-closed with dihydroxyacetone at a high NH$_3$ pressure, and an imidazole alcohol is halogenated and then oxidized to the aldehyde. It should be noted that it has been shown that pressures of over 20 bars are necessary for the ring-closure reaction. Also, the oxidation of the alcohol works in the presence of chromium oxide. Clearly, an oxidation which uses a heavy metal oxide such as chromium oxide is no longer considered to be ecologically responsible, since heavy metal oxides usually are not recyclable.

BROAD DESCRIPTION OF THE INVENTION

An object of the invention is to provide a process which does not have the disadvantages and problems of the prior art as set out above. Other objects and advantages of the invention are set out herein or are obvious herefrom to one ordinarily skilled in the art.

The objects and advantages of the invention are achieved by the process of the invention.

The invention involves a process for preparing 2-substituted 5-chloroimidazole-4-carbaldehydes of the general formula:

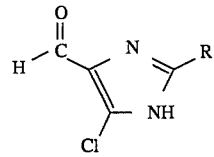

wherein R is hydrogen or is an alkyl group, an alkenyl group, a cycloalkyl group, an arylalkyl group or an aryl group. The process includes; in a first stage, reacting a glycine ester hydrohalide of the general formula:

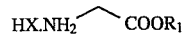

wherein R$_1$ is an alkyl group and X is a halogen atom, with an imidate ester of the general formula:

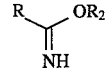

wherein R has the above-mentioned meaning and R$_2$ is an alkyl group, in the presence of a base, to obtain 2-substituted 3,5-dihydroimidazole-4-one of the general formula:

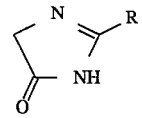

wherein R has the above-mentioned meaning. Next, in a second stage, this intermediate is converted with an N,N-substituted formamide acetal of the general formula:

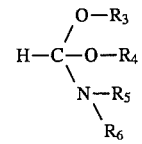

where in R$_3$ and R$_4$ are identical or different and each is an alkyl group or an arylalkyl group, and R$_5$ and R$_6$ are identical or different and each is an alkyl group or an aryl group, into an N,N-substituted aminomethyleneimidazolinone of the general formula:

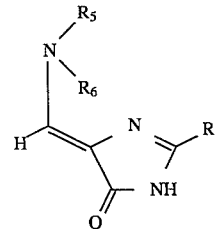

wherein R, R$_5$ and R$_6$ have the above-mentioned meanings. Next, in the third stage, this latter intermediate of general formula VI is chlorinated with phosphorus oxychloride or phosgene to obtain the final product.

Preferably the intermediates of the general formula IV and VI are not isolated. Preferably an alkali metal hydroxide or an alkali metal alkoxide is used as the base in the first stage. Preferably the reaction temperature in the first stage is between −20° C. and 50° C. Preferably the reaction in the second stage is carried out in the presence of an inert solvent at a temperature between −50° C. and 100° C. Preferably the chlorination with phosphorus oxychloride is carried out at a temperature between 50° and 150° C. Preferably the chlorination with phosphorus oxychloride and N,N-dimethylformamide or phosgene and N,N-dimethylformamide is carried out at a temperature between 50° and 150° C.

The invention also includes N,N-substituted aminomethyleneimidazolinones of the general formula:

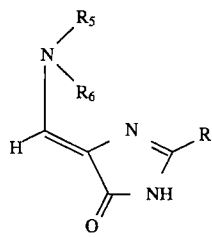

VI wherein R is hydrogen or is an alkyl group, an alkenyl group, a cycloalkyl group, an arylalkyl group or an aryl group and $R_5$ and $R_6$ are identical or different and each is an alkyl group or an aryl group, in the form of the E- or Z-isomer.

Preferably the compound of general formula VI is (Z)-2-butyl-4-dimethylaminomethylene-2-imidazolin-5-one wherein R is butyl, and $R_5$ and $R_6$ are each methyl.

The 2-substituted 5-chloroimidazole-4-carbaldehydes of the general formula I are important starting materials for the preparation of hypotensive pharmaceuticals (U.S. Pat. No. 4,355,040) or of herbicidally active compounds (German Patent No. A 2,804,435).

DETAILED DESCRIPTION OF THE INVENTION

The general names of the groups in the substituents R, $R_1$, $R_2$, $R_3$, $R_4$, $R_5$ and $R_6$ in the general formulae I to VI have the following meaning.

An alkyl group is a straight-chain or branched ($C_1$–$C_6$)-alkyl group, in particular, a methyl group, an ethyl group, a n-propyl group, an i-propyl group, a n-butyl group, a sec.-butyl group, a tert.-butyl group, a pentyl group or one of its isomers, or a hexyl group or one of its isomers. A preferred alkyl group for R is the n-butyl group. A preferred alkyl group for $R_1$, $R_2$, $R_3$, $R_4$, $R_5$ and $R_6$ is a ($C_1$–$C_4$)-alkyl group.

An alkenyl group is a straight-chain or branched ($C_2$–$C_6$)-alkenyl group, such as, a 1-propenyl group, a 2-propenyl group, a 1-butenyl group, a 2-butenyl group, a 3-butenyl group, a pentenyl group or one of its isomers, and a hexenyl group or one of its isomers. A preferred alkenyl group is the 2- or 3-butenyl group.

Examples of cycloalkyl groups are the cyclopropyl group, the cyclobutyl group, the cyclopentyl group and the cyclohexyl group.

The term arylalkyl group means a phenyl-($C_1$–$C_6$) alkyl group, preferably a benzyl group.

The term aryl means phenyl.

Both the arylalkyl group and the aryl group can have one or more substitutents, for example, an alkyl group, halogen, nitro or amino, on their aromatic ring. The term halogen means chlorine, bromine or iodine; the preferred halogen is chlorine.

The first stage of the process of the invention involves reacting a glycine ester hydrohalide of the general formula:

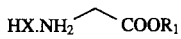 II wherein $R_1$ is an alkyl group and X is a halogen atom, with an imidate ester of the general formula:

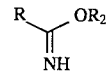

III wherein R has the above-mentioned meaning and $R_2$ is an alkyl group, in the presence of a base, to obtain the 2-substituted 3,5-dihydroimidazole-4-one of the general formula:

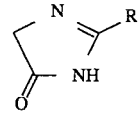

IV wherein R has the above-mentioned meaning.

A procedure is expediently used in which the glycine ester hydrohalide of the general formula II is reacted with the imidate ester of the general formula III in the presence of a base, expediently at a pH of 7 to 12, preferably of 9 to 11.

The glycine ester hydrohalides of the general formula II are commercially available stable compounds.

Suitable bases for use in this reaction are the alkali metal hydroxides, such as, sodium hydroxide and potassium hydroxide, and the alkali metal alkoxides, such as, sodium and potassium methoxide, ethoxide and tert.-butoxide. Advantageously, the base is present dissolved in a suitable solvent. Solvents which are particularly suitable for this purpose are aliphatic alcohols, such as, methanol or ethanol. The imidate ester is expediently also added in the form of a solution in an inert solvent. As a rule, aromatic solvents, such as, toluene, chlorobenzene, or aliphatic solvents, such as, methanol and ethanol, are particularly and highly suitable for this purpose.

The reaction of the reactants, namely, the glycine ester hydrohalide, the imidate ester, and the base advantageously takes place in a stoichiometric ratio of 1:1:1. The reaction temperature is expediently in the range of –20° to 50° C., preferably in the range of 0° to 25° C.

After a reaction time of a few hours, the corresponding intermediate 2-substituted 3,5-dihydroimidazole-4-one of the general formula IV can be isolated in yields greater than 95 percent in a technical manner, as a rule by simple filtration.

Advantageously, however, the intermediate/imidazolinone of the general formula IV is not isolated, but rather the N,N-substituted formamide acetal of the general formula:

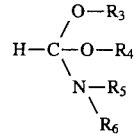

V wherein $R_3$ and $R_4$ are identical or different and each is an alkyl group or an arylalkyl group, and $R_5$ and $R_6$ are identical or different and each is an alkyl group, an arylalkyl group or an aryl group, is directly added to the resultant reaction mixture containing the intermediate of the general formula IV.

Suitable N,N-substituted formamide acetals of the general formula V are the N,N-dimethylformamide dialkyl acetals. N,N-Dimethylformamide dimethyl acetal, in which $R_3$, $R_4$, $R_5$ and $R_6$ are methyl, is particularly preferable.

The reaction in the second stage can be carried out in the presence of an inert solvent, for example, in an aliphatic alcohol, a halogenated hydrocarbon or an aromatic. Therefore, methanol, methylene chloride or toluene can be used with good results. However, it is also possible to carry out the reaction without using an additional solvent, in other words, in the presence of the acetal as a solvent.

The reaction expediently proceeds at a temperature between −50° C. and 100° C., (but preferably at room temperature).

The invention includes the resultant N,N-substituted aminomethyleneimidazolinone of the general formula:

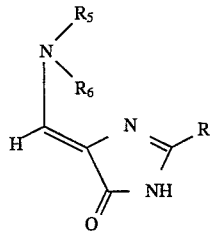

VI wherein R, $R_5$ and $R_6$ have the above-mentioned meanings. These compounds are an important intermediate in the synthesis of the instant invention and are not known in the literature. The N,N-substituted aminomethyleneimidazolinones of the general formula VI can occur as either E- or a Z-isomers. A particularly preferred imidazolinone of the general formula VI is the (Z)-2-butyl derivative wherein R is n-butyl and $R_5$ and $R_6$ each are methyl.

The N,N-substituted aminomethyleneimidazolinone of the general formula VI can be isolated from the reaction mixture in any customary technical manner.

However, without isolation of the intermediate of the general formula VI, it can be chlorinated with phosphorus oxychloride or phosgene in the third and last stage to obtain the final product. The chlorination can be carried out either in the presence of phosphorus oxychloride or in the presence of the so-called Vilsmeier reagent. The so-called Vilsmeier reagent consists of phosphorus oxychloride and N,N-dimethylformamide, or phosgene and N,N-dimethylformamide, expediently in a molar ratio of 1:1 to 4:1. The mentioned chlorinating agents are expediently employed in an excess amount and, thus, simultaneously serve as a solvent. However, the chlorination can be carried out in the presence of an additional inert solvent. The chlorination is expediently carried out at a temperature between 50° and 150° C.

After a reaction time of about 0.5 hours to 4 hours, the corresponding end product 2-substituted 5-chloroimidazole-4-carbaldehyde of the general formula I can be obtained in both good yield and good purity in any customary technical manner. The end product is expediently obtained by treatment of the reaction mixture with water, and by subsequent extraction with a suitable solvent.

EXAMPLE 1

Preparation of
(Z)-2-butyl-4-dimethylaminomethylene-2-imidazolin-5-one VI from 2-butyl-2-imidazolin-5-one IV 2.85 g (content about 92 percent, 22 mmol) of N,N-dimethylformamide dimethyl acetal was added to a solution of 2.80 g (20 mmol) of 2-butyl-2-imidazolin-5-one in 20 ml of methanol. The temperature of the solution rose from 18° to 26° C. After 45 minutes, the solution was concentrated and dried in a high vacuum. 3.88 g of 2-butyl-4-dimethylaminomethylene-2-imidazolin-5-one, having a content of greater than 9 percent according to H-NMR, was obtained. This corresponds to a yield of about 90 percent, based on the 2-butyl-2-imidazolin-5-one. The product could be recrystallized from ethyl acetate. The product had a melting point of 114° to 116.5° C. Other data concerning the product is:

$^1$H-NMR (CDCl$_3$, 400 MHz) 0.95 (3H, t); 1.42 (2H, m); 1.68 (2H, m); 2.53 (2H, t); 3.17 (3H, br s); 3.55 (3H, br s); 7.03 (1H, s); 10.35 (1H, br s).

EXAMPLE 2

Preparation of
(Z)-2-butyl-4-dimethylaminomethylene-2-imidazolin-5-one VI from methyl pentanimidate III 5.00 g (39.42 mmol) of glycine methyl ester hydrochloride was added in a single portion to a solution of 1.59 g (39.42 mmol) of sodium hydroxide in 13 ml of methanol at 0° C. The temperature dropped to −10° C. The mixture was then stirred for 15 minutes and during this time the temperature rose again to 0° C. 4.73 g (39.42 mmol) of methyl pentanimidate was added, and the mixture was stirred at room temperature for 3 hours. Then, during the course of 5 minutes, 5.62 g (43.39 mmol) of N,N-dimethylformamide dimethyl acetal was added, and the reaction mixture was stirred for a further 3 hours. Thereafter, solvent was removed on a Rotavapor, and the residue was treated with 40 ml of CH$_2$Cl$_2$ and 15 ml of water. After phase separation, the organic phase was washed with 10 ml of water, and then the combined H$_2$O phases were washed twice, each time with 20 ml of CH$_2$Cl$_2$. Then, the combined organic phases were dried (MgSO$_4$), filtered, concentrated on the Rotavapor and dried in a high vacuum. 6.70 g of 2-butyl-4-dimethylaminomethylene-2-imidazolin-5-one was obtained, having a content of about 90 percent, according to $^1$H-NMR. This corresponds to a yield of about 78 percent, based on the methyl pentanimidate.

EXAMPLE 3

Preparation of
2-butyl-5-chloroimidazole-4-carbaldehyde I from (Z)-2-butyl-4-dimethylaminomethylene-2-imidazolin-5-one IV A mixture of 1.00 g (5.12 mmol) of 2-butyl-4-dimethylaminomethylene-2-imidazolin-5-one and 3.20 g (20.48 mmol) of POCl$_3$ was heated at 100° C. for 45 minutes. Then, 1.76 g of POCl$_3$ was distilled off on the Rotavapor, and the residue was treated with 6 ml of ethyl acetate. The mixture thus obtained was added to 20 ml of water, and the water was stirred at room temperature for 5 minutes. Then, the pH was adjusted from 0.34 to 7, using 30 percent strength sodium hydroxide solution. The mixture was extracted twice, using 10 ml of ethyl acetate each time. The combined organic phases were dried (MgSO$_4$), filtered and concentrated, and the residue was dried in a high vacuum. 0.89 g of 2-butyl-5-chloroimidazole-4-carbaldehyde was obtained; this product having a purity greater than 95 percent, according to H-NMR. This corresponds to a yield of 93 percent, based on the 2-butyl-4-dimethylaminomethylene-2-imidazolin-5-one.

EXAMPLE 4

Preparation of
(Z)-2-butyl-4-dimethylaminomethylene-2-imidazolin-5-one VI from 2-butyl-2-imidazolin-5-one IV A solution of 5.00 g (35.67 mmol) of 2-butyl-2-imidazolin-5-one and 7.02 g (39.24 mmol) of N,N-dimethylformamide diisopropyl acetal in 25 ml of methylene chloride was stirred at room temperature for 2.5 hours. Then, the solvent was removed on a Rotavapor, and the residue was treated with 40 ml of methylene chloride. The solution thus obtained was washed twice, each time with 10 ml of water, and dried (MgSO₄) and concentrated on the Rotavapor. The residue was then dried in a high vacuum. 5.37 g of 2-butyl-4-dimethylaminomethylene-2-imidazolin-5-one was obtained; the product had a content of greater than 90 percent, according to H-NMR. This corresponds to a yield of about 71 percent, based on the 2-butyl-2-imidazolin-5-one.

EXAMPLE 5

Preparation of (Z)-2-butyl-4-dimethylaminomethylene-2-imidazolin-5-one VI from methyl pentanimidate III 5.00 g (39.42 mmol) of glycine methyl ester hydrochloride was added in a single portion to a solution of 1.59 g (39.42 mmol) of sodium hydroxide in 13 ml of methanol, at 0° C. The temperature dropped to −10° C. Then, the mixture was stirred for 15 minutes. During this time, the temperature rose again to 0° C. 4.73 g (39.42 mmol) of methyl pentanimidate was added, and the mixture was stirred at room temperature for 3 hours. 9.00 g (43.36 mmol) of N,N-dimethylformamide dibutyl acetal then was added, during the course of 5 minutes, and the reaction mixture was stirred for a further 3 hours. Then, the solvent was removed on the Rotavapor, and the residue was treated with 40 ml of CH₂Cl₂ and 15 ml of water. After phase separation, the organic phase was washed with 10 ml of water. The organic phase was dried (MgSO₄), filtered and concentrated on the Rotavapor, and the residue was dried in a high vacuum. 6.92 g of 2-butyl-4-dimethylaminomethylene-2-imidazolin-5-one was obtained; the product had a content of about 80 percent according to H-NMR. This corresponds to a yield of about 72 percent, based on the methyl pentanimidate.

EXAMPLE 6

Preparation of 2-butyl-5-chloroimidazole-4-carbaldehyde I from methyl pentanimidate III 31.72 g (250 mmol) of glycine methyl ester hydrochloride was added in a single portion to a solution of 10.13 g (250 mmol) of sodium hydroxide in 80 ml of methanol at 0° C. The temperature dropped to −10° C. The mixture was stirred for 10 minutes, during which time the temperature rose again to 0° C. 108.25 g (a 26.6 percent strength solution in toluene, 250 mmol) of methyl pentanimidate was added, and the mixture was stirred at room temperature for 3 hours. 35.64 g (about 92 percent strength, 275 mmol) of dimethylformamide dimethyl acetal then was added, during the course of 5 minutes. The reaction mixture was stirred for an additional 3 hours. 200 ml of toluene was added, and methanol and water were removed from the mixture by distillation in vacuo. Of the remaining 203.5 g, 91.68 g (corresponding to 112 mmol of methyl pentanimidate) was initially introduced at room temperature and treated with 65.09 g (416 mmol) of POCl₃. The mixture was heated 15 100° C. for 1.5 hours and then 118.5 g of POCl₃/toluene was distilled off and the residue was treated with 121 ml of ethyl acetate and 408 ml of water. The pH was adjusted to 1, by addition of 18 ml of 30 percent strength sodium hydroxide solution, and the phases were separated. The aqueous phase was extracted twice, each time with 200 ml of ethyl acetate, and the combined organic phases were washed with 200 ml of water, dried (MgSO₄), and filtered and concentrated. The residue was dried in a high vacuum. 14.07 g of 2-butyl-5-chloroimidazole-4-carbaldehyde (HPLC content 79.9 percent) was obtained. This corresponds to a yield of 56 percent, based on the methyl pentanimidate.

What is claimed is:

1. A process for preparing a 2-substituted 5-chloroimidazole-4-carbaldehyde of the formula:

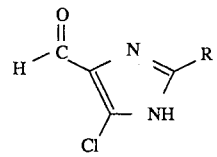

wherein R is hydrogen, an alkyl group, an alkenyl group, a cycloalkyl group, an arylalkyl group or an aryl group, comprising: in a first stage, reacting a glycine ester hydrohalide of the formula:

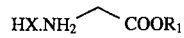

wherein $R_1$ is an alkyl group and X is a halogen atom, with an imidate ester of the formula:

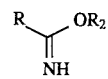

wherein R has the above-mentioned meaning, and $R_2$ is an alkyl group, in the presence of a base to obtain a 2-substituted 3,5-dihydroimidazole-4-one of the formula:

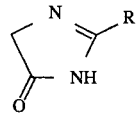

wherein R has the above-mentioned meaning, in a second stage, converting said 2-substituted 3,5-dihydroimidazol-4-one of the formula IV with an N,N-substituted formamide acetal of the formula:

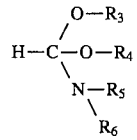

wherein $R_3$ and $R_4$ are identical or different and each is an alkyl group or an arylalkyl group, and $R_5$ and $R_6$ are identical or different and each is an alkyl group or an aryl group, to give an N,N-substituted aminomethyleneimidazolinone of the formula:

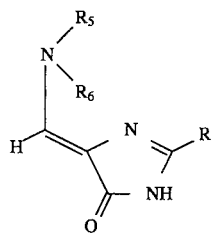

wherein R, $R_5$ and $R_6$ have the above-mentioned meanings, and, finally in the third stage, the N,N-substituted aminomethyleneimidazolinone of the formula VI is chlorinated with phosphorus oxychloride or phosgene to give the final product, namely, the 2-substituted 5-chloroimidazole-4-carbaldehyde of the formula I.

2. The process according to claim 1 wherein said 2-substituted 3,5-dihydroimidazol-4-one of the formula IV and said N,N-substituted aminomethyleneimidazolinone of the formula VI are not isolated.

3. The process according to claim 2 wherein said base, in the first stage, is an alkali metal hydroxide or an alkali metal alkoxide.

4. The process according to claim 3 wherein, in the first stage, the reaction temperature is between −20° C. and 50° C.

5. The process according to claim 4 wherein the reaction in the second stage is carried out in the presence of an inert solvent, at a temperature between −50° C. and 100° C.

6. The process according to claim 5 wherein the chlorination with phosphorus oxychloride is carried out at a temperature between 50° and 150° C.

7. The process according to claim 5 wherein the chlorination with phosphorus oxychloride and N,N-dimethylformamide or phosgene and N,N-dimethylformamide is carried out at a temperature between 50° and 150° C.

8. The process according to claim 1 wherein said base, in the first stage, is an alkali metal hydroxide or an alkali metal alkoxide.

9. The process according to claim 1 wherein, in the first stage, the reaction temperature is between −20° C. and 50° C.

10. The process according to claim 1 wherein the reaction in the second stage is carried out in the presence of an inert solvent at a temperature between −50° C. and 100° C.

11. The process according to claim 1 wherein the chlorination with phosphorus oxychloride is carried out at a temperature between 50° and 150° C.

12. The process according to claim 1 wherein the chlorination with phosphorus oxychloride and N,N-dimethylformamide or phosgene and N,N-dimethylformamide is carried out at a temperature between 50° and 150° C.

* * * * *